(12) United States Patent
Dickie

(10) Patent No.: US 6,295,997 B1
(45) Date of Patent: Oct. 2, 2001

(54) DISPENSER FOR DENTAL FLOSS

(75) Inventor: Robert G. Dickie, Newmarket (CA)

(73) Assignee: Spark Innovations Inc.

( * ) Notice: Subject to any disclaimer, the term of this patent is extended or adjusted under 35 U.S.C. 154(b) by 0 days.

(21) Appl. No.: 09/625,173

(22) Filed: Jul. 25, 2000

(51) Int. Cl.[7] .................................................. A61C 15/04
(52) U.S. Cl. ............................................ 132/321; 206/63.5
(58) Field of Search .................................... 132/322, 323, 132/324, 325, 328, 329, 321; 206/63.5, 408, 409; 242/138, 137.1, 146, 588.6, 598.6; 248/683; D28/65, 66, 67, 68

(56) References Cited

U.S. PATENT DOCUMENTS

| | | | |
|---|---|---|---|
| D. 211,880 | * 8/1968 | Giuseppe | 132/324 |
| D. 345,032 | * 3/1994 | Curtis et al. | D28/64 |
| D. 368,986 | * 4/1996 | Haber et al. | D28/64 |
| D. 381,773 | * 7/1997 | Hemsley, Jr. | D28/64 |
| D. 399,603 | * 10/1998 | Hemsley, Jr. et al. | D28/64 |
| 3,246,815 | * 4/1966 | Aronson | 225/44 |
| 3,480,190 | * 11/1969 | Freedman | 225/33 |
| 4,881,560 | 11/1989 | Blank et al. | |
| 5,054,674 | * 10/1991 | Fortman | 225/6 |
| 5,076,423 | 12/1991 | Russack | |
| 5,156,311 | * 10/1992 | Spencer, Jr. et al. | 225/41 |
| 5,160,077 | * 11/1992 | Sticklin | 225/38 |
| 5,282,563 | 2/1994 | Oliver et al. | |
| 5,649,659 | 7/1997 | Saunders | |
| 5,989,708 | * 11/1999 | Kreckel | 428/354 |

* cited by examiner

Primary Examiner—Todd E. Manahan
Assistant Examiner—Dave Comstock
(74) Attorney, Agent, or Firm—Marks & Clerk

(57) ABSTRACT

A dispenser for dental floss comprises a closed container having a reel of dental floss disposed therein, and having a generally planar back and front face, a pair of opposed side faces, a bottom face, and a top face opposed to the bottom face. There is a hub centrally located in the interior of the closed container, the reel of dental floss is mounted for rotation about the hub when the dental floss is unwound and removed from the reel. A slot is formed in the top face near a first corner of the container, through which slot a strand of dental floss extends so as to be unwound from the reel. A channel is formed at a second corner of the container, at the intersection of the top face and a second side face, and the channel extends between the top face and the second side face. A friction and cutting member comprises a tongue portion which is angled away from a base portion thereof, and is secured in place within the channel. The top face is concave on a centrally located axis extending between the back face and the front face, the concavity being defined by ridges located at the first and second corners. Thus the slot is located in the first ridge at the first corner, and the channel extends through the second ridge at the second corner.

7 Claims, 2 Drawing Sheets

DISPENSER FOR DENTAL FLOSS

FIELD OF THE INVENTION

The present invention relates to a dispenser for dental floss. In particular, the present invention provides a dispenser which may conveniently be, but not necessarily, mounted to a mounting surface. The mounting surface is preferably, but not necessarily, vertical. Especially when mounted to a mounting surface, dental floss may be removed from the dental floss dispenser using but a single hand

BACKGROUND OF THE INVENTION

The use of dental floss is highly recommended by the dental profession as a necessary adjunct to oral hygiene. Indeed, the dental profession recommends that teeth should be flossed using an appropriate dental floss, at least once daily; for example and particularly, as part of the evening ablutions prior to retiring for the night.

Typically, dental floss is sold in a container which serves as the dispenser for the dental floss. Typically, when it is not actually being used to dispense dental floss, the container/dispenser is hidden away from view such as in a drawer, a medicine cabinet, or the like. This generally results in less than diligent flossing practice.

Indeed, recent studies reveal that only about 20 percent of the population of North America flosses regularly, although it is assumed that between 70 percent and up to 90 percent of all households have at least one dental floss container in their possession.

Moreover, it has been noted that there seems to be less of a tendency to want to use a dental floss dispenser which requires it to be held in one hand while dental floss is removed from the dispenser with the other hand, especially in those circumstances where the cutter for the dental floss is exposed and represents a risk to the fingers of the user. Still further it has been noted that most commercially available dental floss dispensers are awkward to use in that the spacing between the opening in the dispenser where the dental floss exits from the interior thereof to the cutter is generally quite small, so that grasping the dental floss in that region so as to remove a length of dental floss from the container is difficult.

For all of these reasons, the present invention provides a dental floss dispenser from which dental floss may be much more easily grasped so as to be removed from the dispenser. In certain embodiments of the present invention, there is provided a dental floss dispenser in which the cutter for the dental floss is hidden from view and is therefore not dangerous to the fingers of a person removing dental floss therefrom.

Still further, in certain embodiments of the dental floss dispenser of the present invention, the dental floss container or dispenser may be mounted on a mounting surface such as a bathroom mirror, inside a medicine cabinet door, on a wall in the bathroom or washroom, or other convenient and visible location. It has been noted that when a dental floss container is conveniently located in such a place and in such a manner that dental floss may be easily removed therefrom, it is more likely to be used, and therefore the practice of flossing one's teeth is much more diligent.

PRIOR ART

Blank et al U.S. Pat. No. 4,881,560, issued Nov. 21, 1989, provides a flat dental floss dispenser which has the approximate size and shape of a credit card. A flat coil of floss is located within the dispenser. However, the cutting blade is quite prominent, thus representing a danger to the fingers of the user. Moreover, to disengage the dental floss from the surface of the cover of the container in the region between the opening through which the dental floss is dispensed and the cutter from which it is removed from the dispenser, requires that the dental floss be effectively pried away from the surface of the container using the fingernails.

Fortman, U.S. Pat. No. 5,054,674, issued Oct. 8, 1991, teaches a dispenser system including a dental floss dispenser which may be retained on or attached to a surface. The dispenser comprises a cassette of dental floss, and a supporting member. The supporting member may be attached to a surface such as a bathroom wall, and may serve other purposes as well such as functioning as a toothbrush holder. However, in this case, notwithstanding that the holder or support member is mounted to a wall, the dental floss dispenser is a separate cassette installed into the holder, and removal of dental floss from the container requires the use of two hands.

Russack, U.S. Pat. No. 5,076,423, issued Dec. 31, 1991, provides a relatively flat, wallet-sized dental floss dispenser. Here, once again, the cutter for the dental floss is prominently mounted over the surface of the container, representing a threat to the fingers of the user. Moreover, once again, the disengaging of dental floss so as to remove a length thereof from the dispenser is awkward, requiring reasonable dexterity with the fingers of the hand of the user.

U.S. Pat. No. 5,156,311, issued Oct. 20, 1992 to Spencer Jr., et al, teaches a dispenser which has a cover and a back section, together with a front section, all of them being molded and hinged together so as to permit the dental floss which is contained therein to be replaced. A shoulder saddle is provided, across which the dental floss is disposed. However, the cutter for the dental floss is prominently located as well on the saddle. Moreover, the configuration of the dispenser, having a hinged cover, requires the use of two hands to remove dental floss from the dispenser, and precludes the possibility that the dispenser can be mounted to such as a vertical, or any, surface.

Oliver et al, U.S. Pat. No. 5,382,563, issued Feb. 1, 1994, teaches a dental floss dispenser having a body which has a spool holder for holding a spool of dental floss at one end, and an exposed cutting member and friction element at the other end of the body. Dental floss is suspended between the spool holder and the cutter, the purpose being so that a user can grasp an exposed portion of floss without contacting any part of the floss dispenser and thereby contaminating the floss dispenser. Particularly, therefore, the floss dispenser described in this patent is one which is intended for use by dentists and dental hygienists, and is not proposed for use by private individuals in their own bathrooms. Various embodiments are illustrated, whereby the dispenser may be mounted on surfaces such as the underside of a table; but in each instance, the purpose is to provide a dental floss dispenser for use by a dentist, a dental assistant, or dental hygienist, in such a manner that the base of the dispenser is not contacted by the fingers of the professional dental caregiver.

Saunders, U.S. Pat. No. 5,649,659 issued Jul. 22, 1997 provides a dental floss dispenser which, again, has essentially the size and shape of a credit card. A spool of floss is wound in the interior of the dispenser, and is dispensed through an opening formed in the dispenser. In one embodiment a recess is formed in the major flat face of the dispenser, having the hole through which the dental floss exits from the interior of the dispenser at one end of the recess, and a cutter/holder disposed at the other end of the recess. In that manner, the cutter, the aperture, and the lead-out portion of dental floss between the opening and the cutter, are all disposed below the major face. In another embodiment, a fan-folded spool of floss is located inside the container, and exits through a hole at one end of the container. A dished top end of the container is provided, across which the lead-out portion of the dental floss extends to an exposed metal cutter assembly.

SUMMARY OF THE INVENTION

The present invention provides a dispenser for dental floss which comprises a closed container having a reel of dental floss disposed therein. The container has a generally planar back face, a generally planar front face, a pair of opposed side faces, a bottom face, and a top face which is opposed to the bottom face.

There is a hub which is centrally located in the interior of the closed container and which extends between the interior surfaces of the front and back faces, in the region occupied by the hub. A reel of dental floss is mounted for rotation about the hub, when dental floss is unwound and removed from the reel.

A slot is formed in the top face near a first corner of the container, through which slot a strand of dental floss extends so as to be unwound from the reel. A channel is formed at the second corner of the container at the intersection of the top face and a second side face, with the channel extending between the top face and the second side face. There is a friction and cutting member which has a tongue portion that is angled away from a base portion thereof, and the friction and cutting member is secured in place within the channel.

The top face is concave on a centrally located axis which extends between the back face and the front face, the concavity thereof being defined by ridges which are located at the first and second corners. Thus, the slot through which the strand of dental floss extends from the interior of the container, is located in a first ridge at the first corner; and the channel in which the friction and cutting member is secured, extends through a second ridge at the second corner.

In general, the top face is sloped forwardly and downwardly in the region of the concavity which is formed therein.

Particularly in the circumstance described immediately above, the back face extends above the top face in the region of the concavity which is formed in the top face.

The channel which is formed at the second corner and which extends through a second ridge at the second corner, is sloped upwardly and rearwardly within the second ridge.

In general, the container of the dental floss dispenser of the present invention may be molded from a plastics material, and the friction and cutting member is formed from metal.

In keeping with a further provision of the present invention, adhesive means may be placed on the substantially planar back face of the container for the dental floss dispenser, so that the dental floss dispenser may be adhesively mounted to a mounting surface.

Generally, the adhesive means comprises a flexible plastic tape which has an adhesive coating on at least a portion of each of the two sides thereof. Typically, the plastic tape is stretchable, and the second portion on each of the two sides of the plastic tape has no adhesive coating thereon, so that the uncoated portion of the flexible plastic tape forms a graspable tab to facilitate the removal of the dental floss dispenser from a mounting surface when it is adhered thereto.

As suggested above, typically the mounting surface is a vertical surface, such as a bathroom mirror, the inside surface of a medicine cabinet door, and so on.

An object of the present invention is to provide such a dispenser for dental floss as described above, which may be easily and inexpensively brought to the market.

Yet a further object of the present invention is to provide such a dental floss dispenser as described above, where the dental floss dispenser may be secured to a mounting surface, and where removal of the dental floss from the dispenser may be easily effected using only a single hand. Typically, the mounting surface to which a dental floss dispenser in keeping with the present invention may be mounted, is a vertical surface.

BRIEF DESCRIPTION OF THE DRAWINGS

The novel features which are believed to be characteristic of the present invention, as to its structure, organization, use and method of operation, together with further objectives and advantages thereof, will be better understood from the following drawings in which a presently preferred embodiment of the invention will now be illustrated by way of example. It is expressly understood, however, that the drawings are for the purpose of illustration and description only and are not intended as a definition of the limits of the invention. Embodiments of this invention will now be described by way of example in association with the accompanying drawings in which.

Figure 1:
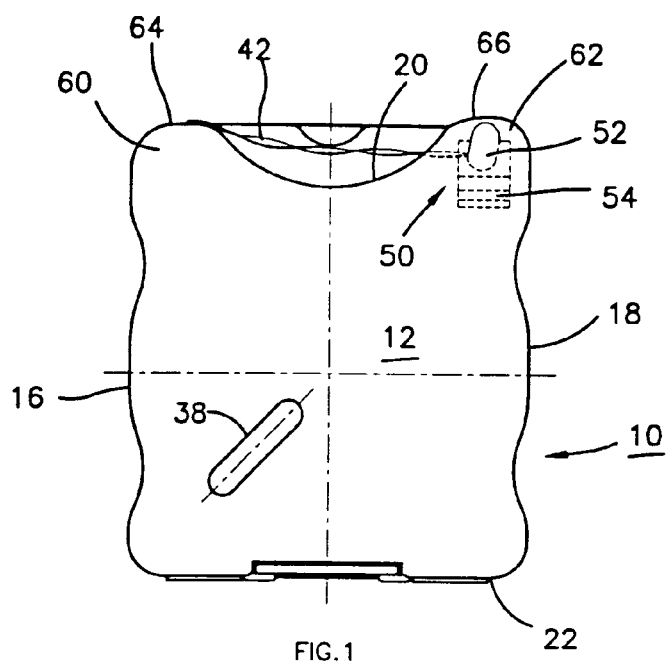
FIG. 1 is a front view of a dental floss dispenser in keeping with the present invention.

DETAILED DESCRIPTION OF THE PREFERRED EMBODIMENT:

Referring now to FIGS. 1 through 6, a dental floss dispenser 10 in keeping with the present invention is shown. The dental floss dispenser comprises a closed container which has a reel of dental floss 24 disposed therein. The container has a generally planar back face 14, a generally planar front face 12, a pair of opposed side faces 16, 18, a bottom face 22, and a top face 20 which is opposed to the bottom face 22.

There is a hub 40 which is centrally located in the interior of the closed container, and which extends between the interior surfaces of the front and back faces 12, 14. Typically, the hub 40 may comprise a spool 42, mounted on a spindle 44.

Clearly, the reel of dental floss 24 is mounted for rotation about the hub 40, when the dental floss 42 is unwound and removed from the reel 24.

A slot 30 is formed in the top face 20 near a first corner 60, which is in the region of the intersection of the side face 16 and the top face 20. The dental floss 42 extends through the slot 30, so as to be unwound from the reel 24.

There is a channel 32 which is formed at a second corner 62, in the region of the intersection between the top face 20 and the second side face 18. The channel extends between the top face 20 and the second side face 18.

A friction and cutting member 50, which comprises a tongue portion 52 that is angled away from a base portion 54, is secured within the channel 32.

There is a slot or opening 38 on the front face of the container so that the amount of dental floss remaining on the reel 24 can be determined.

The top face 20 is concave on a centrally located axis 25 which extends between the back face 14 and the front face 12, the concavity being defined by ridges 64 and 66 which are located in the general region of the first corner 60 and the second corner 62, respectively.

Thus, the slot 30 is located in the first ridge 64, and the channel 32 extends through the second ridge 66.

Figure 2:
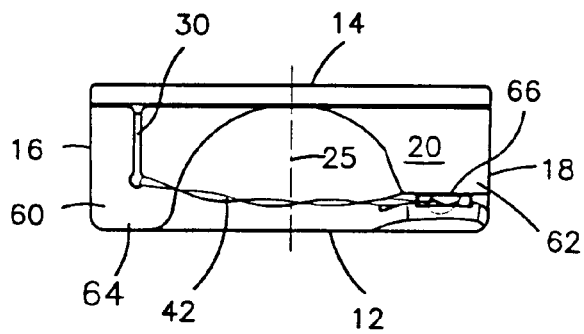
FIG. 2 is a top view of a dental floss dispenser in keeping with the present invention.

Typically, as shown in FIG. 2, the concave portion of the top face 20 is broader at the front of the dispenser than at the rear of the dispenser. Also, as shown in FIG. 6, the top face 20 is sloped forwardly and downwardly in the region of the concavity which is formed therein.

Figure 5:
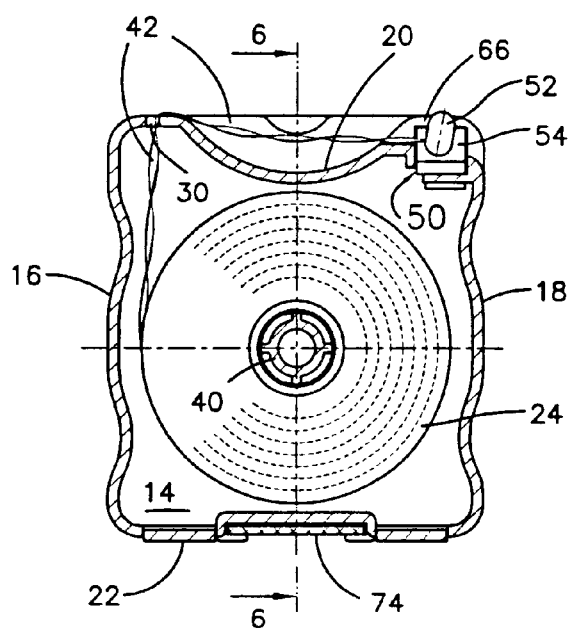
FIG. 5 is a sectional view taken on the line 5—5 in FIG. 6.
Figure 6:
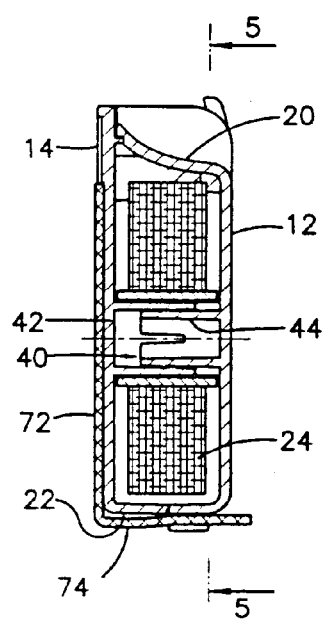
FIG. 6 is an elevation sectional view taken on the line 6—6 in FIG. 5.

Moreover, as can be clearly seen in FIGS. 1, 5, and 6, the back face 14 typically extends above the top face 20, in the region of the concavity which is formed at the top face 20.

Figure 3:
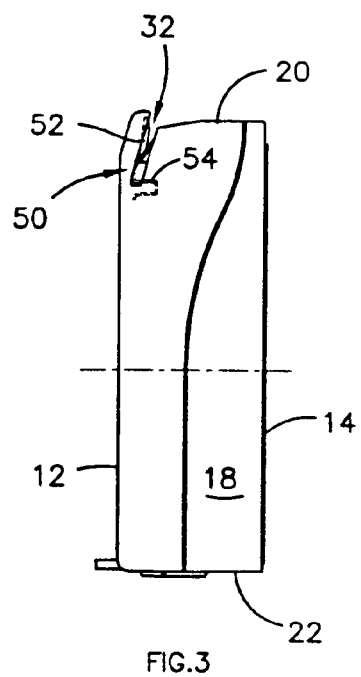
FIG. 3 is a side view, from the right side as seen in FIG. 1.
Figure 4:
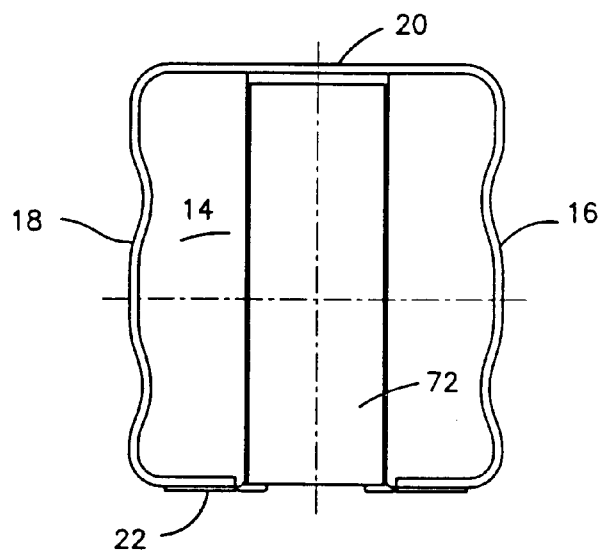
FIG. 4 is a back view of a dental floss dispenser in keeping with the present invention.

Still further, as can be clearly seen in FIG. 3, the channel 32 is sloped upwardly and rearwardly within the second ridge 66.

Typically, any dental floss dispenser in keeping with the present invention is comprised of a container which is molded from a suitable plastics material, as will be evident to persons skilled in the art; and the friction and cutting member is formed from metal, usually by stamping.

Finally, a further aspect of the present invention is discussed. That is, any dental floss dispenser in keeping with the present invention may further comprise adhesive means 72 disposed on the substantially planar back face 14. The adhesive means 72 provides means whereby the dental floss dispenser of the present invention may be adhesively mounted to a mounting surface. Such mounting surface may be any convenient, substantially planar surface, such as a counter top, the side wall of a drawer, etc.; however, most usually, the mounting surface is a vertical surface such as a bathroom mirror, the inside surface of the door of a medicine cabinet, and so on.

Typically, the adhesive means 72 is a flexible flat plastic tape, which has an adhesive coating on at least a portion of each of the two sides thereof. The coating on the surface of the flexible plastic tape which is adjacent the back face 14 of the container thereby adheres the adhesive means 72 to the dental floss dispenser. The adhesive on the other side of the flexible tape is generally provided with a release cover (not shown) whereby the dental floss dispenser may be adhered to a mounting surface when desired, but not until. This is clear, for example, from an examination of FIGS. 4, 5, and 7.

Also, typically, the flexible plastic tape which comprises the adhesive means 72 is formed so as to have a second portion on each of the two sides thereof which has no adhesive coating thereon. This uncoated portion of the flexible plastic tape thereby forms a graspable tab 74 which may be grasped by the fingers so as to facilitate the removal of the dispenser from a mounting surface when it is adhered thereto. Such removal would occur, for example, when the reel of dental floss 24 in the interior of the dental floss dispenser has been exhausted so that it is necessary to replace the dental floss dispenser with a new one—or in some instances, to replace the reel of dental floss inside the dental floss container.

A particular flexible plastic tape having the characteristics as described above is one which is brought to the market by 3-M Company in association with its trade mark COMMAND™.

Other modifications and alterations may be used in the design and manufacture of the apparatus of the present invention without departing from the spirit and scope of the accompanying claims.

Throughout this specification and the claims which follow, unless the context requires otherwise, the word "comprise", and variations such as "comprises" or "comprising", will be understood to imply the inclusion of a stated integer or step or group of integers or steps but not to the exclusion of any other integer or step or group of integers or steps.

Moreover, the word "substantially" when used with an adjective or adverb is intended to enhance the scope of the particular characteristic; e.g., substantially planar is intended to mean planar, nearly planar and/or exhibiting characteristics associated with a planar element.

What is claimed is:

1. A dispenser for dental floss comprising:

a closed container having a reel of dental floss disposed therein, said container having a generally planar back face, a generally planar front face, a pair of opposed side faces, a bottom face, and a top face opposed to said bottom face;

a hub centrally located in the interior of the closed container and extending between the interior surfaces of said front and back faces, in the region occupied by said hub, and a reel of dental floss being mounted for rotation about said hub when said dental floss is unwound and removed from said reel;

a slot formed in said top face near a first corner of said container, through which slot a strand of dental floss extends so as to be unwound from said reel;

a channel formed at a second corner of said container at the intersection of said top face and a second side face, said channel extending between said top face and said second side face; and adhesive means on the substantially planar back face, whereby a dental floss dispenser may be adhesively mounted to a mounting surface;

wherein said friction and cutting member is secured in place within said channel;

wherein said channel extends through said second ridge at said second corner;

a friction and cutting member comprising a tongue portion which is angled away from a base portion thereof, and being secured in place at a second corner of said container at the intersection of said top face and a second side face;

wherein said top face is concave on a centrally located axis extending between said back face and said front face, the concavity thereof being defined by ridges located at said first and second corners; and wherein said slot is located in a first ridge at said first corner.

2. The dental floss dispenser of claim 1, wherein said top face is sloped forwardly and downwardly in the region of the concavity formed therein.

3. The dental floss dispenser of claim 2, wherein said back face extends above said top face in the region of the concavity formed in said top face.

4. The dental floss dispenser of claim 1, wherein said channel is sloped upwardly and rearwardly within said second ridge.

5. The dental floss dispenser of claim 1, wherein said container is molded from a plastics material, and said friction and cutting member is formed from metal.

6. The dental floss dispenser of claim 1, wherein said adhesive means comprises a flexible plastic tape having an adhesive coating on at least a portion of each of the two sides thereof.

7. The dental floss dispenser of claim 6, wherein said flexible plastic tape is stretchable, and wherein a second portion on each of the two sides thereof has no adhesive coating therein; and wherein the uncoated portion of the flexible plastic tape forms a graspable tab to facilitate removal of said dispenser from a mounting surface when adhered thereto.

* * * * *